United States Patent [19]

Kleemann et al.

[11] Patent Number: 5,235,057
[45] Date of Patent: Aug. 10, 1993

[54] AMINODIOL DERIVATIVES

[75] Inventors: Heinz-Werner Kleemann, Kelsterbach; Rainer Henning, Hattersheim am Main; Hansjörg Urbach, Kronberg/Taunus, all of Fed. Rep. of Germany

[73] Assignee: Hoechst Aktiengesellschaft, Frankfurt am Main, Fed. Rep. of Germany

[21] Appl. No.: 723,223

[22] Filed: Jun. 28, 1991

[30] Foreign Application Priority Data

Jul. 2, 1990 [DE] Fed. Rep. of Germany ....... 4021007

[51] Int. Cl.$^5$ ................. C07D 401/06; C07D 277/22; C07D 409/06; C07D 317/72
[52] U.S. Cl. .................................... 546/269; 546/283; 548/202; 548/205; 548/300.7; 548/313.1; 548/315.1; 548/311.1; 549/60; 549/331; 549/341; 549/451
[58] Field of Search ................. 549/331, 341, 351, 60, 549/451; 546/269, 283; 548/202, 205, 336

[56] References Cited

FOREIGN PATENT DOCUMENTS 0349247 1/1990 European Pat. Off. .
0355597 2/1990 European Pat. Off. .
0370454 5/1990 European Pat. Off. .
89/8990 8/1990 South Africa .

OTHER PUBLICATIONS

Chemical Abstracts, vol. 109, No. 13, 110855j (Sep. 26, 1988).
Chemical Abstracts, Vol. 111, No. 23, 214356e (Dec. 4, 1989).
Chemical Abstracts, vol. 113, No. 3, 24297e (Jul. 16, 1990).
Chemical Abstracts, vol. 113, 231702y (Dec. 17, 1990).

*Primary Examiner*—C. Warren Ivy
*Assistant Examiner*—A. A. Owens
*Attorney, Agent, or Firm*—Finnegan, Henderson, Farabow, Garrett & Dunner

[57] ABSTRACT

The invention relates to compounds of the formula

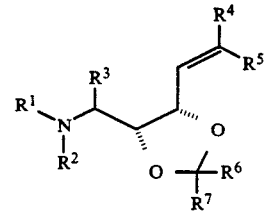

in which $R^1$ and $R^2$ are identical or different and are hydrogen or aralkyl, $R^3$ is alkyl, cycloalkyl or cycloalkylalkyl, $R^4$ and $R^5$ are identical or different and are hydrogen, alkyl, cycloalkyl, cycloalkylalkyl, aryl, aralkyl or a heterocyclic radical and $R^6$ and $R^7$ are identical or different and are hydrogen, alkyl, cycloalkyl, cycloalkylalkyl, aryl or arlkyl or $R^6$ and $R^7$, together with the carbon atom carrying them, are cycloalkyl. The novel compounds are prepared by a carbonyl olefination according to Wittig. They are intermediates for the preparation of pharmaceuticals, in particular of inhibitors of renin and HIV protease.

1 Claim, No Drawings

AMINODIOL DERIVATIVES

The invention relates to compounds of the formula I

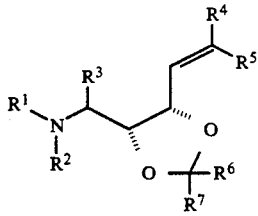

in which $R^1$ and $R^2$ are identical or different and are hydrogen, 1-[($C_6$–$C_{14}$)-aryl]-($C_1$–$C_6$)-alkyl, 1,1-di-[($C_6$–$C_{14}$)-aryl]-($C_1$–$C_6$)-alkyl or 1,1,1-tri-[($C_6$–$C_{14}$)-aryl]-($C_1$–$C_6$)-alkyl, it being possible for aryl in each case to be substituted by one or two identical or different radicals from the series comprising ($C_1$–$C_6$)alkyl, ($C_1$–$C_4$)-alkoxy and halogen;

$R^3$ is ($C_1$–$C_{12}$)-alkyl, mono-, bi- or tricyclic ($C_3$–$C_{18}$)-cycloalkyl or mono-, bi- or tricyclic ($C_3$–$C_{18}$)-cycloalkyl-($C_1$–$C_6$)-alkyl, where the cycloalkyl moiety is in each case optionally substituted by ($C_1$–$C_6$)-alkyl;

$R^4$ and $R^5$ are identical or different and are hydrogen, ($C_1$–$C_{12}$)-alkyl, ($C_3$–$C_{12}$)-cycloalkyl, ($C_3$–$C_{12}$)-cycloalkyl-($C_1$–$C_6$)-alkyl, ($C_6$–$C_{14}$)-aryl, ($C_6$–$C_{14}$)-aryl-($C_1$–$C_6$)-alkyl, it being possible for aryl in each case to be substituted by one, two or three radicals from the group comprising ($C_1$–$C_6$)-alkyl, ($C_1$–$C_4$)-alkoxy and halogen, het or het-($C_1$–$C_6$)-alkyl, where het is a 5-, 6- or 7-membered heterocyclic ring which is optionally fused to benzene and can be aromatic, partly hydrogenated or completely hydrogenated and which as a heteroelement contains one or two identical or different radicals from the group comprising N, O, S, NO, SO and $SO_2$ and which can be substituted by one or two identical or different radicals from the group comprising ($C_1$–$C_6$)-alkyl, ($C_1$–$C_4$)-alkoxy and halogen; and $R^6$ and $R^7$ are identical or different and are hydrogen, ($C_1$–$C_{12}$)-alkyl, ($C_3$–$C_{12}$)-cycloalkyl, ($C_3$–$C_{12}$)-cycloalkyl-($C_1$–$C_6$)-alkyl, ($C_6$–$C_{14}$)-aryl, or ($C_6$–$C_{14}$)-aryl-($C_1$–$C_6$)-alkyl, it being possible for aryl in each case to be substituted by one, two or three identical or different radicals from the group comprising ($C_1$–$C_6$)-alkyl, ($C_1$–$C_4$)-alkoxy and halogen; or $R^6$ and $R^7$, together with the carbon atom carrying them, are ($C_3$–$C_{12}$)-cycloalkyl;

and their salts.

Alkyl can be straight-chain or branched. The same applies to radicals derived therefrom, such as alkoxy.

Cycloalkyl is understood as meaning, for example, cyclopropyl, cyclobutyl, cyclopentyl, cyclohexyl or cycloheptyl.

A radical indicated as het preferably has one of the following meanings: pyridyl, thiazolyl, thienyl, pyranyl, benzofuryl, isobenzofuryl, furyl, pyrrolyl, imidazolyl, pyrazinyl, indazolyl, quinolyl, isoquinolyl, phthalazinyl, pyrimidinyl, pyrazinyl, indolizinyl, isoindolyl, indolyl, quinoxalinyl, quinazolinyl, cinnolinyl, oxazolyl, isoxazolyl or isothizolyl. The radicals can be aromatic, partly hydrogenated or completely hydrogenated. They can be substituted by one or two identical or different radicals from the group comprising ($C_1$–$C_6$)-alkyl, ($C_1$–$C_4$)-alkoxy and halogen.

($C_6$–$C_{14}$)-aryl is understood as meaning, for example, phenyl, naphthyl or biphenylyl; phenyl is preferred.

Halogen is fluorine, chlorine, bromine or iodine.

Preferred compounds of the formula I are those in which $R^1$ and $R^2$ are identical or different and are hydrogen, 1-[($C_6$–$C_{14}$)-aryl]-($C_1$–$C_6$)-alkyl or 1,1-di-[($C_6$–$C_{14}$)-aryl]-($C_1$–$C_6$)-alkyl, it being possible for aryl in each case to be substituted by one or two identical or different radicals from the series comprising ($C_1$–$C_6$)-alkyl, ($C_1$–$C_4$)-alkoxy and halogen;

$R^3$ is ($C_1$–$C_6$)-alkyl, mono-, bi- or tricyclic ($C_3$–$C_{18}$)-cycloalkyl or mono-, bi- or tricyclic ($C_3$–$C_{18}$)-cycloalkyl-($C_1$–$C_3$)-alkyl;

$R^4$ and $R^5$ are as defined above; and $R^6$ and $R^7$ are identical or different and are hydrogen, ($C_1$–$C_{12}$)-alkyl, ($C_3$–$C_{12}$)-cycloalkyl or ($C_3$–$C_{12}$)-cycloalkyl-($C_1$–$C_6$)-alkyl; or these radicals, together with the carbon atom carrying them, are ($C_3$–$C_{12}$)-cycloalkyl;

and their salts.

Particularly preferred compounds of the formula I are those in which $R^1$ and $R^2$ are identical or different and are hydrogen, benzyl, 2-, 3- or 4-methylbenzyl, 2-, 3- or 4-methoxybenzyl, 2-, 3- or 4-chlorobenzyl, 1-phenylethyl or diphenylmethyl;

$R^3$ is methyl, ethyl, n-propyl, n-butyl, 2-methylpropyl, 2-ethylbutyl, cyclopentylmethyl, cyclohexylmethyl or cycloheptylmethyl;

$R^4$ and $R^5$ are as defined above; and $R^6$ and $R^7$ are identical and are hydrogen or ($C_1$–$C_4$)-alkyl, or these radicals, together with the carbon atom carrying them, are ($C_5$–$C_{17}$)-cycloalkyl;

and their salts.

Very particularly preferred compounds of the formula I are those in which $R^1$ and $R^2$ are identical or different and are hydrogen, benzyl, 2-, 3- or 4-methylbenzyl, 2-, 3- or 4-methoxybenzyl, 1-phenylethyl or diphenylmethyl;

$R^3$ is methyl, ethyl, n-propyl, n-butyl, 2-methylpropyl, 2-ethylbutyl, cyclopentylmethyl, cyclohexylmethyl or cycloheptylmethyl;

$R^4$ and $R^5$ are identical or different and are hydrogen, ($C_1$–$C_4$)-alkyl, ($C_5$–$C_7$)-cycloalkyl, ($C_5$–$C_7$)-cycloalkyl-($C_1$–$C_3$)-alkyl, phenyl, benzyl, 2-pyridyl, 3-pyridyl, 4-pyridyl, 2-thiazolyl, 4-thiazolyl, 5-thiazolyl, 2-thienyl, 3-thienyl, 1-methylimidazol-2-yl, 1-methylimidazol-4-yl or 1-methylimidazol-5-yl; and $R^6$ and $R^7$ are identical and are hydrogen or ($C_1$–$C_4$)-alkyl, or these radicals, together with the carbon atom carrying them, are ($C_5$–$C_7$)-cycloalkyl;

and their salts.

The invention furthermore relates to a process for the preparation of compounds of the formula I, which comprises reacting a compound of the formula IV

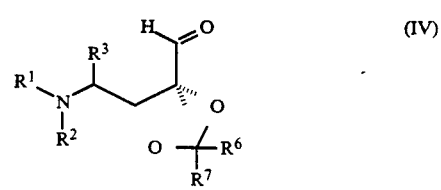

in which the radicals $R^1$, $R^2$, $R^3$, $R^6$ and $R^7$ are as defined above, with a phosphorane of the formula V

in which $R^4$ and $R^5$ are as defined above and $R^8$, $R^9$ and $R^{10}$ are identical or different aryl radicals, preferably phenyl.

To prepare a compound of the formula IV, suitably protected furanose-N-glycosides such as D-mannofuranose-N-glycosides, L-gulofuranose-N-glycosides, D-talofuranose-N-glycosides or L-allofuranose-N-glycosides can be used as starting materials. The reaction with a carbon nucleophile such as a Grignard compound or an alkyllithium compound in a solvent which is inert to these nucleophiles, such as diethyl ether, di-n-butyl ether, MTB, DIP, THF, tetrahydropyran, formaldehyde dimethyl acetal or DME, at a temperature between −30° C. and the boiling point of the solvent, preferably between −10° C. and +35° C., if desired with the aid of ultrasound, yields the derivative of the formula II

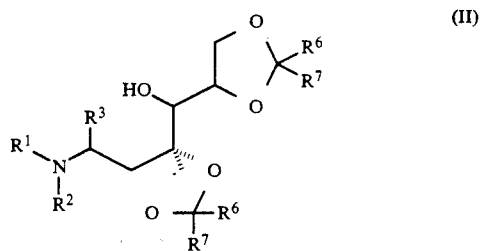

in which the radicals $R^1$, $R^2$, $R^3$, $R^6$ and $R^7$ are as defined above.

Reaction with acids in suitable solvents such as water, methanol or ethanol at a temperature of 0° C. to 65° C., preferably at 0° C. to 30° C., yields derivatives of the formula III

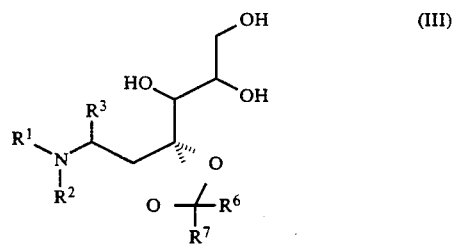

in which the radicals $R^1$, $R^2$, $R^3$, $R^6$ and $R^7$ are as defined above.

Suitable acids are carboxylic acids such as acetic acid or sulfonic acids such as p-toluenesulfonic acid.

Reaction with oxidants cleaving 1,2-diols, such as $NaIO_4$ or $Pb(OAc)_4$, $Ca(OCl)_2$, $Bu_4NIO_4$, $MnO_2$, $Tl^{3+}$, $Co^{3+}/O_2$ or $H_5IO_6$ in inert solvents such as water, diethyl ether, di-n-butyl ether, MTB, DME, DIP, THF or dioxane at 0° C. to 50° C., preferably at 0° C. to 30° C., yields the aldehyde of the formula IV, in which the radicals $R^1$, $R^2$, $R^3$, $R^6$ and $R^7$ are as defined above.

Wittig reaction with a suitable phosphorane in an inert solvent such as diethyl ether, di-n-butyl ether, MTB, DIP, THF, DME or dioxane at −30° C. up to the boiling point of the solvent, preferably between 0° C. and 30° C., yields the title compounds of the formula I. The aldehyde of the formula IV can also be reacted with the anion of a suitable phosphine oxide with the formation of the title compound (Horner; see Krauch, Kunz, Reactionen der Organischen Chemie (Reactions of Organic Chemistry), Hüthig Verlag Heidelberg 1976, page 241).

In some combinations of the radicals $R^1$-$R^7$, those radicals $R^1$ and $R^2$ which are favorable for the synthesis of the derivatives of the formula II are unfavorable for the synthesis of the derivatives of the formula IV. In such cases, reprotection is expediently carried out:

For this, the derivative of the formula III is subjected either to hydrogenation with hydrogen and Pd/C or to transfer hydrogenation, for example with ammonium formate or cyclohexene and Pd/C. Suitable solvents are alcohols such as methanol and ethanol. The temperature is expediently chosen to be between −20° C. and the boiling point of the solvent, 0° C. up to the boiling point being preferred.

The crude product from the hydrogenation is then reacted with suitable electrophiles, carrying the new $R^1$ and $R^2$ radicals, in a solvent such as diethyl ether, tetrahydrofuran or t-butanol using an auxiliary base such as triethylamine, ethyldiisopropylamine or N-methylpiperidine. Suitable electrophiles are, for example, chlorides, bromides, iodides, methanesulfonates, toluenesulfonates or trifluoromethanesulfonates. To increase the reaction rate when using chlorides or bromides, anhydrous sodium iodide can expediently be added. The reaction temperature is chosen to be between 0° C. and the boiling point of the solvent, preferably between 20° C. and the boiling point.

The compounds of the formula I according to the invention are useful intermediates for the preparation of pharmaceuticals, in particular of inhibitors of renin and HIV protease. Inhibitors for whose synthesis the compounds of the formula I can advantageously be used are described, for example, in FEBS Lett. 230, 38 (1988), J. Med. Chem. 31, 2264 (1988), J. Med. Chem. 31, 2277 (1988), Biochem. Biophys. Res. Commun. 146 959 (1987) and EP-A-370,454.

List of the abbreviations used:

| | |
|---|---|
| TLC | Thin layer chromatography |
| DCI | Desorption chemical ionization |
| DIP | Diisopropyl ether |
| DME | 1,2-Dimethoxyethane |
| EA | Ethyl acetate |
| FAB | Fast atom bombardment |
| Hep | n-Heptane |
| M | Molecular peak |
| MeOH | Methanol |
| MS | Mass spectrum |
| MTB | Methyl tert.-butyl ether |
| NEM | N-ethylmorpholine |
| R.T. | Room temperature |
| M.p. | Melting point |
| THF | Tetrahydrofuran |

The Examples below are used to illustrate the present invention, without it being restricted thereto:

EXAMPLE 1

N,N-dibenzyl-[1-cyclohexylmethyl-(2,3-isopropylidene)-2(R),3(S)-dihydroxy-5-(2-pyridyl)-pent-4-en-1-yl]amine 1.3 g of N,N-dibenzyl-[1-cyclohexylmethyl-(2,3-isopropylidene)-2(R),3(R),4(R),5(R),6-pentahyydroxy]-hexylamine are dissolved in 65 ml of diethyl ether and 25 ml of 1 M $KH_2PO_4$ solution are added 2.7 g of $NaIO_4$ in 50 ml of $H_2O$ are then added at room temperature and the mixture is stirred at this temperature for 4 days 50 ml of 10% aqueous $Na_2SO_3$ solution are then added, the mixture is extracted 3 times with 100 ml of diethyl ether, the organic phase is dried over $Na_2SO_4$ and the solvent is removed in vacuo. The residue is finally dried at room temperature in an oil pump vacuum for a further 3 h and the crude aldehyde is obtained 1.1 g of 2-picolyltriphenylphosphonium chloride are then suspended in 15 ml of THF (anhydrous) and 0.3 g of potassium t-butylate is added at room temperature. After 3.5 h, the mixture is cooled to 0° C. and the above crude aldehyde is added dropwise in 10 ml of THF. The reaction mixture is stirred at room temperature for 18 h, poured into 100 ml of saturated aqueous $NaHCO_3$ solution and extracted 3 times with 100 ml of EA, the extract is dried over $Na_2SO_4$ and the solvent is removed in vacuo. Chromatography on silica gel using diisopropyl ether yielded 980 mg of the title compound as a colorless oil, nearly exclusively trans according to NMR.

$R_f(DIP) = 0.31$   MS (DCI):511 (M + 1)

EXAMPLE 1a

N,N-dibenzyl-[1-cyclohexylmethyl-(2,3-isopropylidene)-2(R),3(R),4(R),5(R),6-pentahydroxy]hexylamine 5.2 g of N-benzhydryl-[1-cyclohexylmethyl-(2,3-isopropylidene)-2(R),3(R),4(R),5(R),6-pentahydroxy]hexylamine are dissolved in 200 ml of methanol, 6.8 g of ammonium formate and 1.0 g of 10% Pd/C are added and the mixture is stirred at room temperature for 3 hours. The catalyst is filtered off, the methanol is removed in vacuo, and the residue is taken up in 200 ml of EA/200 ml of satd. aqueous $Na_2CO_3$ solution and extracted twice more with 200 ml of EA. The extract is dried over $Na_2SO_4$ and the solvent is removed in vacuo. The residue is taken up in 100 ml of THF (anhydrous), 2.6 ml of benzyl bromide, 3.7 ml of diisopropylethylamine and 6.4 g of NaI (anhydrous) are added and the mixture is heated under reflux for 16 hours. It is then poured into 250 ml of satd. aqueous $NaHCO_3$ and extracted 3 times with 150 ml of EA. The extract is dried over $Na_2SO_4$ and the solvent is then removed in vacuo. Chromatography on silica gel using MTB yields 4.2 g of the title compound as a white foam.

$R_f(MTB) = 0.42$   MS (DCI):498 (M + 1)

EXAMPLE 1b

N-benzhydryl-[1-cyclohexylmethyl-(2,3-isopropylidene)-2(R),3(R),4(R),5(R),6-pentahydroxy]hexylamine 1.7 g of N-benzhydryl-[1-cyclohexylmethyl,(2,3-,5,6-diisopropylidene)-2(R),3(R),4(R),5(R),6-pentahydroxy]-hexylamine are dissolved in 70 ml of methanol and 1.7 g of p-toluenesulfonic acid are added. The mixture is stirred at room temperature for 5 h and then added to 300 ml of satd. aqueous $Na_2CO_3$ solution, the methanol is removed in vacuo and the residue is extracted 3 times with 150 ml of EA. The extract is dried over $Na_2SO_4$, the solvent is removed in vacuo and the residue is chromatographed on silica gel using EA. 1.2 g of the title compound are obtained as a white foam.

$R_f(EA) = 0.41$   MS(FAB):484 (M + 1)

EXAMPLE 1c

N-benzhydryl-[1-cyclohexylmethyl-(2,3-5,6-diisopropylidene)-2(R),3(R),4(R),5(R),6-pentahydroxy]hexylamine 520 mg of lithium wire (1% Na, $\phi$ 3.2 mm) are initially introduced into 12 ml of diethyl ether (anhydrous) under argon and about 40 $\mu$l of cyclohexylmethyl bromide are injected in at room temperature and the mixture is stirred until the reaction starts, which is shown by turbidity. The mixture is then cooled to $-10°$ C. and a further 4.2 ml of cyclohexylmethyl bromide in 6 ml of diethyl ether are added dropwise The mixture is stirred at $-10°$ C. to $0°$ C. for 6 h, then cooled to $-30°$ C. and benzhydrylamino-D-mannofuranoside diacetonide in 20 ml of diethyl ether cooled to $-30°$ C. is added rapidly (exothermic!). After 15 min, the reaction is already complete by TLC. After stirring at room temperature for 1 h, the lithium residues are filtered off, the reaction solution is added to 150 ml of satd. aqueous $NaHCO_3$ solution and the mixture is extracted 3 times with 100 ml of ethyl acetate. It is dried over $Na_2SO_4$, the solvent is removed in vacuo and the residue is chromatographed on 500 g of silica gel using diisopropyl ether/toluene 1:5.

4.6 g of the title compound are obtained as a colorless oil $R_f(DIP) = 0.31$   MS(DCI):511 (M + 1)

EXAMPLE 1d

Benzhydrylamino-mannofuranoside diacetonide 10 g of D(+)-mannose and about 10 mg of p-toluenesulfonic acid are suspended in 40 ml of 2,2-dimethoxypropane and the mixture is stirred at 40° C. for 1 h. A clear solution is formed during the course of this. 10 ml of benzhydrylamine are added and the mixture is heated to reflux for 24 h. A further 10 ml of 2,2-dimethoxypropane and 2 ml of benzhydrylamine are then added and the mixture is heated at reflux for a further 18 h. Volatile components are removed in vacuo, the residue is taken up in 100 ml of EA and the mixture is washed 3 times with 100 ml of $NaHCO_3$ solution. It is dried over $Na_2SO_4$, the solvent is removed in vacuo and the residue is chromatographed on silica gel using DIP/toluene 1:5. 17 g of the title compound are obtained as pale yellow crystals, m.p.: 82°–84° C.

$R_f(DIP/toluene\ 1:3) = 0.41$   MS(DCI):426 (M + 1)

Alternative synthesis of the title compound of Example 1c:

EXAMPLE 1e

N-benzhydryl-[1-cyclohexylmethyl-(2,3-,5,6-diisopropylidene)-2(R),3(R),4(R),5(R),6-pentahydroxy]hexylamine 1.8 g of benzhydrylamino-mannofuranoside diacetonide and 1.2 ml of cyclohexylmethyl bromide are dissolved in 40 ml of formaldehyde dimethyl acetal (distilled from K/Na alloy) and reacted at 20°–40° C. under argon in an ultrasonic bath with 115 mg of lithium wire (3.2 mm, about 1% Na) for 3.5 h 115 mg of lithium wire and 1.2 ml of cyclohexylmethyl bromide are then added again and the mixture is reacted at 40°–60° C. for a further 1 h. The reaction mixture is poured into 200 ml of NaHCO₃ solution and extracted 3 times with 100 ml of MTB. The extract is dried over Na₂SO₄, and the solvent is removed in vacuo and chromatographed on silica gel using DIP/toluene 1:3. 1.1 g of the title compound are obtained as a colorless oil.

EXAMPLE 2

N,N-dibenzyl-[1-cyclohexylmethyl-(2,3-isopropyliden)-2(R),3(S)-dihydroxy-5-methyl-hexene(4)-1-yl]amine The compound can be prepared according to example 1.

The following physical properties were found:

$R_f$(DIP/HEP 1:10) = 0,33    MS(DCI):462 (M + 1)

We claim:
1. A compound of the formula I

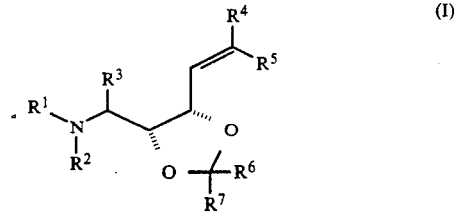

in which
$R^1$ and $R^2$ are identical or different and are hydrogen, benzyl, 2-, 3- or 4-methylbenzyl, 2-, 3- or 4-methoxybenzyl, 1-phenylethyl or diphenylmethyl;

$R^3$ is methyl, ethyl, n-propyl, n-butyl, 2-methylpropyl, 2-ethylbutyl, cyclopentylmethyl, cyclohexylmethyl or cycloheptylmethyl;

$R^4$ and $R^5$ are identical or different and are hydrogen, $(C_1-C_4)$-alkyl, $(C_5-C_7)$-cycloalkyl, $(C_5-C_7)$-cycloalkyl-$(C_1-C_3)$-alkyl, phenyl, benzyl, 2-pyridyl, 3-pyridyl, 4-pyridyl, 2-thiazolyl, 4-thiazolyl, 5-thiazolyl, 2-thienyl, 3-thienyl, 1-methylimidazol-2-yl, 1-methyl-imidazol-4-yl or 1-methylimidazol-5-yl; and $R^6$ and $R^7$ are identical and are hydrogen or $(C_1-C_4)$-alkyl, or these radicals, together with the carbon atom carrying them, are $(C_5-C_7)$-cycloalkyl;

or a salt thereof.

* * * * *